(12) United States Patent
Harish et al.

(10) Patent No.: US 6,503,556 B2
(45) Date of Patent: Jan. 7, 2003

(54) METHODS OF FORMING A COATING FOR A PROSTHESIS

(75) Inventors: Sameer Harish, Fremont, CA (US); Steven Wu, Santa Clara, CA (US); Deborra Sanders Millare, San Jose, CA (US); Judy Guruwaiya, San Jose, CA (US); Stephen Pacetti, San Jose, CA (US); Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/751,691

(22) Filed: Dec. 28, 2000

(65) Prior Publication Data

US 2002/0122877 A1 Sep. 5, 2002

(51) Int. Cl.[7] .............................. B05D 1/36; B05D 3/06; B05D 7/20; A61L 27/00; A61L 33/10
(52) U.S. Cl. .................. 427/2.24; 427/2.25; 427/2.28; 427/2.3; 427/553; 427/554; 427/555; 427/556; 427/258; 427/261; 427/287; 427/407.1; 427/409
(58) Field of Search ................... 427/2.24, 2.25, 427/2.28, 2.3, 2.31, 553, 554, 555, 556, 258, 261, 287, 407.1, 409

(56) References Cited

U.S. PATENT DOCUMENTS

| 2,072,303 | A | 3/1937 | Herrmann et al. ........ 128/335.5 |
|---|---|---|---|
| 4,733,665 | A | 3/1988 | Palmaz ........................ 128/343 |
| 4,800,882 | A | 1/1989 | Gianturco .................... 128/343 |
| 4,886,062 | A | 12/1989 | Wiktor ........................ 128/343 |
| 4,977,901 | A | 12/1990 | Ofstead ....................... 128/772 |
| 5,328,471 | A | 7/1994 | Slepian ....................... 604/101 |
| 5,383,928 | A | * 1/1995 | Scott et al. ..................... 623/1 |
| 5,464,650 | A | 11/1995 | Berg et al. .................... 427/2.3 |
| 5,575,818 | A | * 11/1996 | Pinchuk .......................... 623/1 |
| 5,578,073 | A | 11/1996 | Haimovich et al. ............ 623/1 |
| 5,605,696 | A | 2/1997 | Eury et al. ................... 424/423 |
| 5,628,730 | A | 5/1997 | Shapland et al. ............. 604/21 |
| 5,649,977 | A | 7/1997 | Campbell ....................... 623/1 |
| 5,667,767 | A | 9/1997 | Greff et al. ............... 424/9.411 |

(List continued on next page.)

FOREIGN PATENT DOCUMENTS

| EP | 0 665 023 | 8/1995 | |
|---|---|---|---|
| EP | 0 970 711 | 1/2000 | |
| JP | 11299901 | 2/1999 | .......... A61M/29/02 |

(List continued on next page.)

OTHER PUBLICATIONS

Barath et al., *Low Dose of Antitumor Agents Prevents Smooth Muscle Cell Proliferation After Endothelial Injury*; JACC vol. 13, No. 2, Feb. 1989:252A (Abstract).

(List continued on next page.)

*Primary Examiner*—Shrive P. Beck
*Assistant Examiner*—Jennifer Kolb Michener
(74) *Attorney, Agent, or Firm*—Squire Sanders & Dempsey L.L.P.

(57) ABSTRACT

Methods of forming a coating onto an implantable device or endoluminal prosthesis, such as a stent, are provided. The coating may be used for the delivery of an active ingredient. The coating may have a selected pattern of interstices for allowing a fluid to seep through the coating in the direction of the pattern created.

14 Claims, 3 Drawing Sheets

U.S. PATENT DOCUMENTS

| | | | |
|---|---|---|---|
| 5,670,558 A | | 9/1997 | Onishi et al. ............... 523/112 |
| 5,700,286 A | * | 12/1997 | Tartaglia et al. ............... 623/1 |
| 5,716,981 A | | 2/1998 | Hunter et al. ............... 514/449 |
| 5,800,392 A | | 9/1998 | Racchini ..................... 604/96 |
| 5,824,049 A | | 10/1998 | Ragheb et al. ................ 623/1 |
| 5,830,178 A | | 11/1998 | Jones et al. .................... 604/49 |
| 5,837,313 A | | 11/1998 | Ding et al. ................ 427/2.21 |
| 5,851,508 A | | 12/1998 | Greff et al. .............. 424/9.411 |
| 5,865,814 A | | 2/1999 | Tuch ......................... 604/265 |
| 5,869,127 A | * | 2/1999 | Zhong ...................... 427/2.12 |
| 5,873,904 A | | 2/1999 | Ragheb et al. ................. 623/1 |
| 5,897,911 A | * | 4/1999 | Loeffler ..................... 427/2.25 |
| 5,971,954 A | | 10/1999 | Conway et al. ............... 604/96 |
| 5,980,928 A | | 11/1999 | Terry ......................... 424/427 |
| 5,980,972 A | | 11/1999 | Ding ........................ 427/2.24 |
| 6,010,530 A | | 1/2000 | Goiceochea ................... 623/1 |
| 6,015,541 A | | 1/2000 | Greff et al. ................ 424/1.25 |
| 6,096,070 A | | 8/2000 | Ragheb et al. ................. 623/1 |
| 6,139,573 A | * | 10/2000 | Sogard et al. ............. 623/1.13 |
| 6,153,252 A | | 11/2000 | Hossainy et al. ............ 427/2.3 |
| 6,165,212 A | * | 12/2000 | Dereume et al. .......... 623/1.13 |
| 6,251,136 B1 | * | 6/2001 | Guruwaiya et al. ........ 623/1.46 |

FOREIGN PATENT DOCUMENTS

| | | | |
|---|---|---|---|
| WO | WO 91/12846 | 9/1991 | |
| WO | WO 97/45105 | 12/1997 | |
| WO | WO 99/63981 | 12/1999 | |
| WO | WO 00/12147 | 3/2000 | |
| WO | WO 00/38590 | 7/2000 | ............. A61F/2/06 |
| WO | WO 00/38754 | 7/2000 | ........... A61L/31/10 |
| WO | WO 00/42949 | * 7/2000 | ............. A61F/2/06 |
| WO | WO 00/56247 | 9/2000 | ............. A61F/2/06 |
| WO | WO 00/57818 | 10/2000 | ............. A61F/2/06 |
| WO | WO 00/64506 | 11/2000 | |
| WO | WO 00/71052 | 11/2000 | ............. A61F/2/06 |
| WO | WO 01/01890 | 1/2001 | |
| WO | WO 01/45763 | 6/2001 | |

OTHER PUBLICATIONS

Matsumaru et al., *Embolic Materials for Endovascular Treatment of Cerebral Lesions*; J. Biomater. Sci. Polymer Edn, vol. 8, No. 7 (1997), pp. 555–569.

Miyazaki et al., *Antitumor Effect of Implanted Ethylene–Vinyl Alcohol Copolymer Matrices Containing Anticancer Agents on Ehrlich Ascites Carcinoma and P388 Leukemia in Mice*, Chem. Pharm. Bull. 33(6)(1985), pp. 2490–2498.

Miyazawa et al., *Effects of Pemirolast and Tranilast on Intimal Thickening After Arterial Injury in the Rat*; J. Cardiovasc. Pharmacol. (1997), pp. 157–162.

Ohsawa et al., *Preventive Effects of an Antiallergic Drug, Pemirolast Potassium, on Restenosis After Percutaneous Transluminal Coronary Angioplasty*; American Heart Journal (Dec. 1998), pp. 1081–1087.

Shigeno, *Prevention of Cerebrovascular Spasm by Bosentan, Novel Endothelin Receptor*; Chemical Abstract 125:212307 (1996).

* cited by examiner

METHODS OF FORMING A COATING FOR A PROSTHESIS

BACKGROUND OF THE INVENTION

1. Field of the Invention

The invention relates to implantable devices or endoluminal prostheses, such as stents, and methods of coating such devices.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, an expandable, intraluminal prosthesis, one example of which is a stent, is implanted in the lumen to maintain the vascular patency.

Stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in the patent literature disclosing stents that have been applied in PTCA procedures include U.S. Pat. No. 4,733,665 issued to Pahnaz, U.S. Pat. No. 4,800,882 issued to Gianturco, and U.S. Pat. No. 4,886,062 issued to Wiktor. Mechanical intervention via stents has reduced the rate of restenosis as compared to balloon angioplasty. Yet, restenosis is still a significant clinical problem with rates ranging from 20–40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

Depending on the physiological mechanism targeted, the therapeutic substance may be required to be released at an efficacious concentration for an extended duration of time. Increasing the quantity of the therapeutic substance in the polymeric coating can lead to poor coating mechanical properties, inadequate coating adhesion, and overly rapid rate of release. Increasing the quantity of the polymeric compound by producing a thicker coating can perturb the geometrical and mechanical functionality of the stent, as well as limit the procedure for which the stent can be used.

It is desirable to increase the residence time of a substance at the site of implantation, at a therapeutically useful concentration, without the application of a thicker coating. It is also desirable to be able to increase the quantity of the therapeutic substance carried by the polymeric layer without perturbing the mechanical properties of the coating, such as adhesion of the polymer to the stent substrate.

SUMMARY OF THE INVENTION

The present invention provides a method of forming a coating for a prosthesis, e.g., a stent. The method includes depositing a polymeric sheath over at least a portion of a prosthesis. The prosthesis has a plurality of interconnected struts separated by gaps and a longitudinally extending central bore for allowing a fluid to travel through the prosthesis. The method further includes exposing the polymeric sheath to a temperature not greater than about the melting temperature of the polymer to form a coating for the prosthesis. The method can further include removing a portion of the coating positioned over some of the gaps to form a pattern of interstices dispersed between the struts for allowing a fluid that flows through the central bore to seep through the coating.

In one embodiment, the coating contains an active ingredient. In other embodiments, the coating contains radiopaque elements or radioactive isotopes.

Also provided is a method for increasing an amount of a polymeric coating on a stent having struts separated by gaps, without increasing the thickness of the coating. The method includes inserting a stent having a plurality of interconnected struts separated by gaps into a polymeric sheath. The method further includes exposing the polymeric sheath to a temperature not greater than about the melting temperature of the polymer to form a coating for the stent. The coating covers the struts and the gaps between the struts so as to increase the quantity of the coating supported by the stent without increasing the thickness of the coating on the stent. The method can also include removing a portion of the coating deposited over at least one of the gaps to create an opening in the coating. The size of the opening is smaller than the size of the gap. The opening allows a fluid, such as blood, to travel through the coating from within the stent.

DETAILED DESCRIPTION OF THE EMBODIMENTS

Some of the various embodiments of the present invention are illustrated by FIGS. 1–6. The Figures have not been drawn to scale, and the size of the various regions have been over or under emphasized for illustrative purposes.

Examples of the Prosthesis

Figure 1:
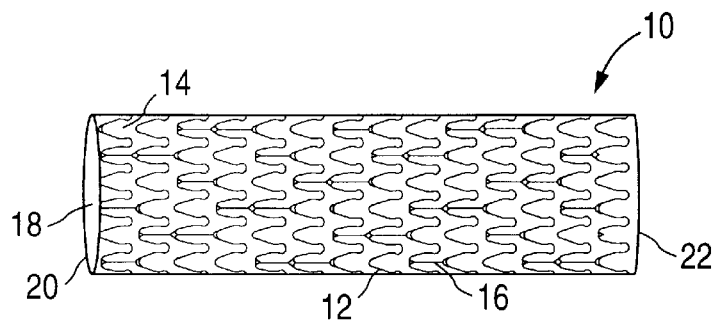
FIG. 1 illustrates a side view of an implantable device.

The device or prosthesis used in conjunction with the compositions described below may be any suitable device used for the release of an active ingredient or for the incorporation of radiopaque or radioactive materials, examples of which include self-expandable stents, balloon-expandable stents, grafts, and stent-grafts. Referring to FIG. 1, a body of a stent 10 is formed from a plurality of struts 12. Struts 12 are separated by gaps 14 and may be interconnected by connecting elements 16. Struts 12 can be connected in any suitable configuration and pattern. Stent 10 is illustrated having an outer surface (tissue-contacting surface) and an inner surface. A hollow, central bore 18 extends longitudinally from a first end 20 to a second end 22 of stent 10.

Stent 10 can be made of a metallic material or an alloy such as, but not limited to, stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Stent 10 made from bioabsorbable or biostable polymers could also be used with the embodiments of the present invention. A polymeric device should be compatible with the selected compositions described below.

Composition for Forming a Sheath

The embodiments of the composition for forming a sheath are prepared by conventional methods wherein all components are combined, then blended. More particularly, in accordance with one embodiment, a predetermined amount of a polymeric compound is added to a predetermined amount of a mutually compatible solvent. The polymeric compound can be added to the solvent at ambient pressure and, if applicable, under anhydrous atmosphere. If necessary, gentle heating and stirring and/or mixing can be employed to effect dissolution of the polymer into the solvent, for example 12 hours in a water bath at about 60° C.

"Polymer," "poly," and "polymeric" are defined as compounds that are the product of a polymerization reaction and are inclusive of homopolymers, copolymers, terpolymers etc., including random, alternating, block, and graft variations thereof. Particular care should be taken to ensure that the polymer employed in the composition will not be adversely affected by the heat treatment applied to the sheath formed from the composition as described below. The polymer chosen should be a polymer that is biocompatible. The polymer may be bioabsorbable or biostable. Bioabsorbable polymers that may be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. In addition, biostable polymers with a relatively low chronic tissue response such as polyurethanes, silicones, and polyesters may be used. Other polymers may also be used if they can be dissolved and cured or polymerized on stent 10 such as polyolefins, polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Ethylene vinyl alcohol is functionally a very suitable choice of polymer. The copolymer adheres well to metal surfaces, such as stainless steel, and has illustrated the ability to expand with a stent without any significant detachment of the copolymer from the surface of the stent. Ethylene vinyl alcohol copolymer, commonly known by the generic name EVOH or by the trade name EVAL, refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percentage of ethylene of from about 27% to about 47%. Typically, 44 mole percent ethylene is suitable. Ethylene vinyl alcohol copolymers are available commercially from companies such as Aldrich Chemical Company, Milwaukee, Wis., or EVAL Company of America, Lisle, Ill., or can be prepared by conventional polymerization procedures that are well known to one of ordinary skill in the art.

The solvent should be capable of placing the polymer into solution at the concentration desired in the composition. Examples of solvents include, but are not limited to, dimethylsulfoxide (DMSO), chloroform, acetone, water (buffered saline), xylene, acetone, methanol, ethanol, 1-propanol, tetrahydrofuran, 1-butanone, dimethylformamide, dimethylacetamide, cyclohexanone, and N-methyl pyrrolidinone. With the use of low ethylene content, e.g., 29 mol %, ethylene vinyl alcohol copolymer, a suitable solvent is iso-propylalcohol (IPA) admixed with water (e.g., 1:1).

By way of example, the polymer can comprise from about 15% to about 34%, more narrowly from about 20% to about 25% by weight of the total weight of the composition, and the solvent can comprise from about 66% to about 85%, more narrowly from about 75% to about 80% by weight of the total weight of the composition.

In another embodiment, sufficient amounts of an active ingredient are dispersed in the blended composition of the polymer and the solvent. The active ingredient may be in true solution or saturated in the blended composition. If the active ingredient is not completely soluble in the composition, operations including mixing, stirring, and/or agitation can be employed to effect homogeneity of the residues. The active ingredient may be added so that the dispersion is in fine particles. The mixing of the active ingredient can be conducted at ambient pressure, at room temperature, and if applicable in an anhydrous atmosphere, such that supersaturating the active ingredient is not desired.

As with the selection of the polymer, particular care should be taken to ensure that the active ingredient employed in the composition will not be adversely affected by the heat treatment applied to the sheath formed from the composition as described below. Otherwise, the active ingredient may be any substance capable of exerting a therapeutic or prophylactic effect in the practice of the present invention. Examples of such active ingredients include antiproliferative, antineoplastic, antiinflammatory, antiplatelet, anticoagulant, antifibrin, antithrombin, antimitotic, antibiotic, and antioxidant substances as well as combinations thereof.

A suitable example of an antiproliferative substance is actinomycin D, or derivatives and analogs thereof. Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. Exposure of the composition to the active ingredient is not permitted to adversely alter the active ingredient's composition or characteristic. Accordingly, the particular active ingredient is selected for mutual compatibility with the blended polymer-solvent composition.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required can depend upon factors such as the particular circumstances of the patient; the nature of the trauma; the nature of the therapy desired; the time over which the ingredient administered resides at the treatment site; and if other bioactive substances are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

By way of example, the polymer can comprise from about 14% to about 33%, more narrowly from about 20% to about 25% by weight of the total weight of the composition, the solvent can comprise from about 33% to about 85%, more narrowly from about 50% to about 70% by weight of the total weight of the composition, and the active ingredient can comprise from about 1% to about 50%, more narrowly from about 10% to about 25% by weight of the total weight of the composition. More than 40% by weight of the active ingredient could adversely affect characteristics that are desirable in the polymeric coating, such as controlled release of the active ingredient. Selection of a specific weight ratio of the polymer and solvent is dependent on factors such as, but not limited to, the material from which the device is made, the geometrical structure of the device, and the type and amount of the active ingredient employed. The particular weight percentage of the active ingredient mixed within the composition depends on factors such as duration of the release, cumulative amount of release, and release rate that is desired.

In accordance with another embodiment, the polymeric composition includes radiopaque elements or radioactive isotopes. Examples of radiopaque elements include, but are not limited to, gold, tantalum, and platinum. An exemplary radioactive isotope is $P^{32}$. Sufficient amounts of radiopaque elements or radioactive isotopes may be dispersed in the composition. By dispersed it is meant that the substances are not present in the composition as agglomerates or flocs. In some compositions, certain substances will disperse with ordinary mixing. Otherwise, the substances can be dispersed in the composition by high shear processes such as ball mill, disc mill, sand mill, attritor, rotor stator mixer, or ultrasonication—all such high shear dispersion techniques being well known to one of ordinary skill in the art. Biocompatible dispersing agents in the form of surfactants, emulsifiers, or stablilizers may also be added to the composition to assist in dispersion.

Forming a Sheath from the Composition

Figure 2:
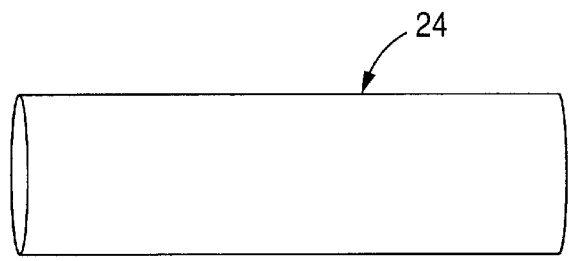
FIG. 2 illustrates a side view of a sheath.

Referring now to FIG. 2, a sheath 24 is formed from the embodiments of the above-described composition, which may contain an active ingredient. The inner diameter of sheath 24 should be slightly larger than the outer diameter of stent 10 to allow sheath 24 to be fitted over stent 10 as described below. Sheath 24 can have any suitable thickness so long as the thickness does not compromise properties that are critical for achieving optimum performance. Such properties include low susceptibility to defects or tearing, the ability to be deposited on stent 10, good flexibility, and the ability to allow stent 10 to expand for engagement against the vessel wall. By way of example and not limitation, the thickness can be in the range of about 0.001 inch to about 0.002 inch, or about 25.4 microns to about 50.8 microns.

Sheath 24 may be formed using any suitable method known to one of ordinary skill in the art. By example, and not limitation, sheath 24 may be extruded in the form of a generally tubular structure using conventional extrusion techniques, which are well known to those of ordinary skill in the art. Alternatively, a flat sheet of uniform thickness may be formed from the composition using, for example, a casting blade, then rolled into a generally tubular structure, and sealed at its ends to form sheath 24.

Formation of a Coating for a Stent

Figure 3:
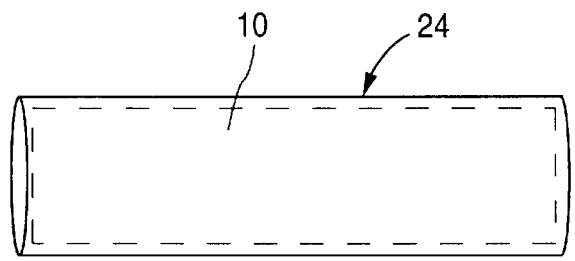
FIG. 3 illustrates the implantable device of FIG. 1 after the sheath of FIG. 2 has been deposited thereon.

Referring to FIG. 3, sheath 24 is fitted over stent 10 and exposed to a heat treatment. Heat may be applied to stent 10 via a convection oven, a heat gun, or by any other suitable heat source.

With the use of the above-described thermoplastic polymers such as ethylene vinyl alcohol copolymer, polycaprolactone, poly(lactide-co-glycolide), and poly(hydroxybutyrate), sheath 24 should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the polymeric coating to the metallic surface of a stent. Stent 10 should be exposed to the heat treatment for any suitable duration of time that will allow for the polymer to take on a somewhat sticky consistency without complete liquefaction. Particular care should be exercised to ensure that an active ingredient contained in sheath 24 is not exposed to a temperature that may adversely alter the active ingredient's composition or characteristic.

Table 1 lists the $T_g$ and $T_m$ for some of the polymers used in the embodiments of the composition for forming sheath 24 and, ultimately, coating 26. $T_g$ and $T_m$ of polymers are attainable by one of ordinary skill in the art. The cited exemplary temperature is provided by way of illustration and is not meant to be limiting.

TABLE 1

| Polymer | $T_g$ (° C.) | $T_m$ (° C.) | Exemplary Temperature (° C.) |
|---|---|---|---|
| EVOH | 55 | 165 | 70 |
| polycaprolactone | −60 | 60 | 50 |
| ethylene vinyl acetate (e.g., 33% vinyl acetate content) | 36 | 63 | 45 |
| Polyvinyl alcohol | 75–85* | 200–220* | 75 |

*Exact temperature depends on the degree of hydrolysis which is also known as the amount of residual acetate.

Figure 4:
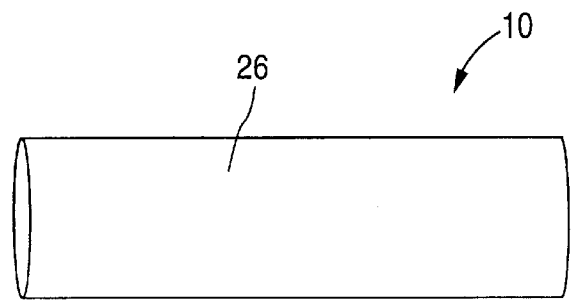
FIG. 4 illustrates the implantable device of FIG. 3 following a heat treatment to form a coating thereon.

The above-described heat treatment allows the polymeric material of sheath 24 to adhere to struts 12 of stent 10 to form a coating 26, as illustrated in FIG. 4. Vacuum conditions may be employed to ensure that coating 26 adheres uniformly to stent 10. Coating 26 covers struts 12 as well as gaps 14 between struts 12.

As mentioned above, conventional coating methods coat the struts of a stent, leaving voids in the coating over the gaps between the struts. By forming coating 26 to cover struts 12 as well as gaps 14 between struts 12, the present invention allows an increased amount of the polymeric coating to be present on stent 10 without increasing the thickness of the coating. Accordingly, the amount of therapeutic substance is increased concomitantly.

Formation of an Optional Primer Layer

An optional primer layer can be formed on the outer surface of stent 10 prior to the insertion of stent 10 within sheath 24. The presence of an active ingredient in a polymeric matrix typically interferes with the ability of the matrix to adhere effectively to the surface of the device. An increase in the quantity of the active ingredient reduces the effectiveness of the adhesion. High drug loadings of, for example, 10–40% by weight in the coating may significantly hinder the retention of the coating on the surface of the device. The primer layer serves as a functionally useful intermediary layer between the surface of the device and an active ingredient-containing sheath. The primer layer provides for an adhesive tie between sheath 24 and stent 10—which, in effect, would also allow for the quantity of the active ingredient in coating 26 formed from sheath 24 to be increased without compromising the ability of coating 26 to be effectively contained on stent 10 during delivery and, if applicable, expansion of stent 10.

To form an optional primer layer, the surfaces of stent 10 should be clean and free from contaminants that may be introduced during manufacturing. However, the surfaces of stent 10 require no particular surface treatment to retain the applied coating. Metallic surfaces of stents can be, for example, cleaned by an argon plasma process as is well known to one of ordinary skill in the art. A primer layer may be formed on stent 10 by applying a primer composition to stent 10 and then removing the solvent from the applied primer composition to form the desired primer layer on stent 10.

The primer composition typically includes a polymer dissolved in a solvent. Suitable polymers and solvents were described above with reference to the composition for forming sheath 24 and are equally applicable here. Application of the primer composition can be accomplished by any conventional method, such as by spraying the primer composition onto stent 10 or immersing stent 10 in the primer composition. Such application methods are understood by one of ordinary skill in the art.

The solvent is removed from the primer composition by allowing the solvent to evaporate. The evaporation can be induced by heating stent 10 at a predetermined temperature for a predetermined period of time. For example, stent 10 can be heated at a temperature of about 60° C. for about 12 hours to about 24 hours. The heating can be conducted in an anhydrous atmosphere and at ambient pressure. The heating can, alternatively, be conducted under a vacuum condition. It is understood that essentially all of the solvent will be removed from the primer composition but traces or residues can remain. Upon removal of the solvent from the primer composition, a primer layer is formed on stent 10.

Patterning the Coating to Form Interstices Therein

Figure 5A:
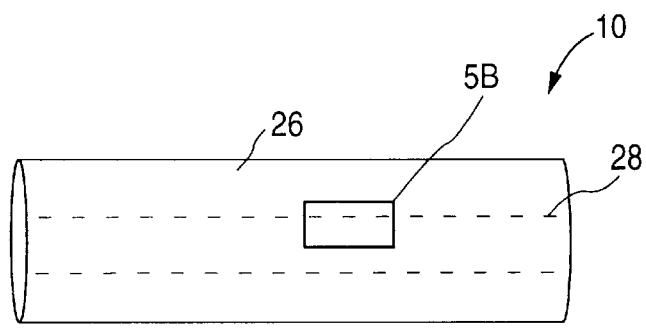
FIG. 5A illustrates the implantable device of FIG. 4 after a pattern of interstices has been created within the coating.
Figure 5B:
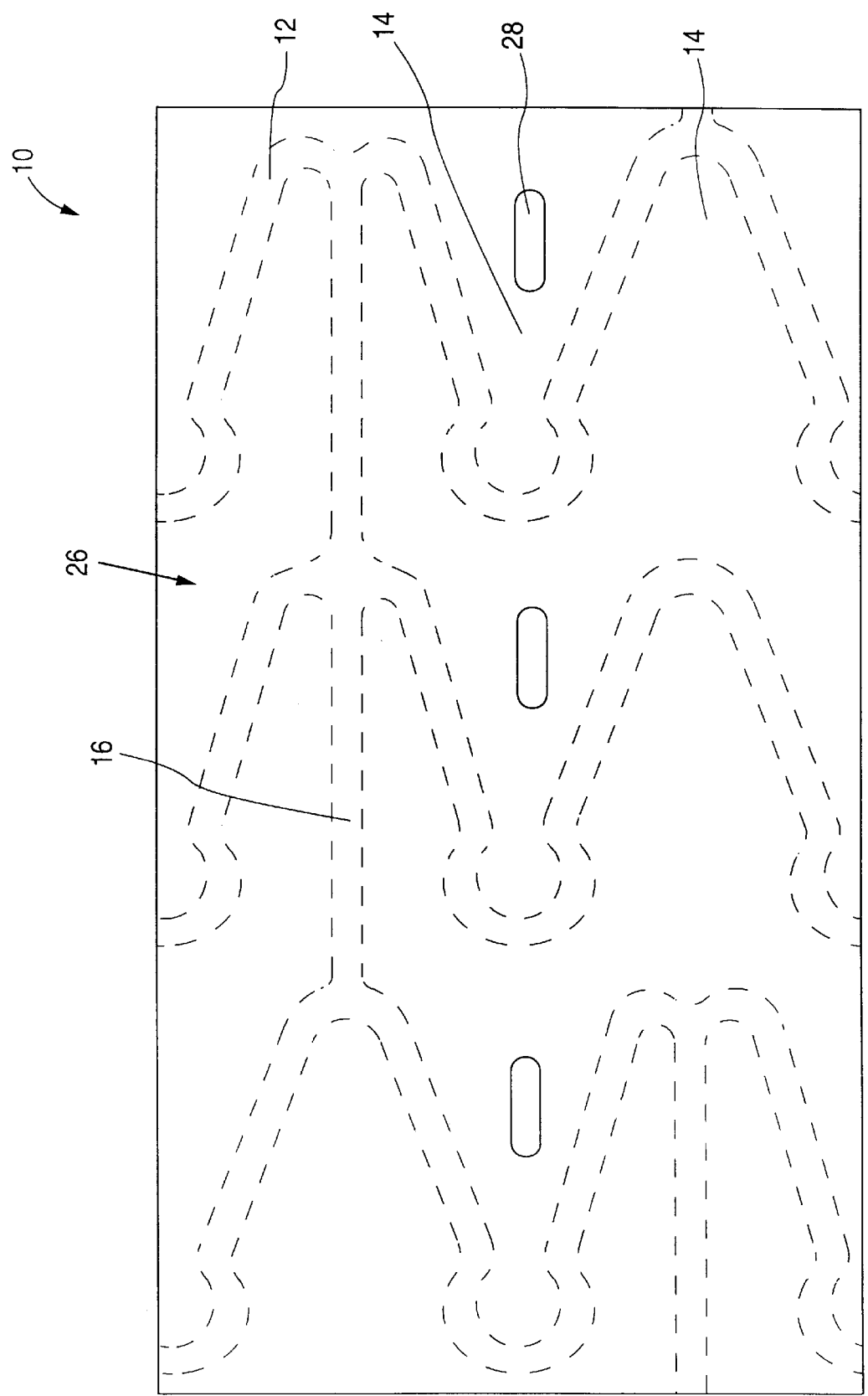
FIG. 5B illustrates an enlarged view of region 5B of the implantable device in FIG. 5A.

As illustrated in FIGS. 5A and 5B, coating 26 may be patterned such that portions of coating 26 positioned over at least some of gaps 14 are removed to yield a pattern of interstices 28 dispersed between struts 12. Such patterning of coating 26 may be accomplished, for example, by exposing designated portions of coating 26 to the discharge of a laser, such as an excimer laser. Application of a laser discharge to form patterns can be performed by one of ordinary skill in the art.

Interstices 28 may be of any suitable size and shape and are typically smaller than the gap 14 in which they are created. Interstices 28 may be interspersed between struts 12 in any pattern. The pattern of interstices 28 created depends, in part, on the application for which stent 10 is to be utilized.

Figure 6:
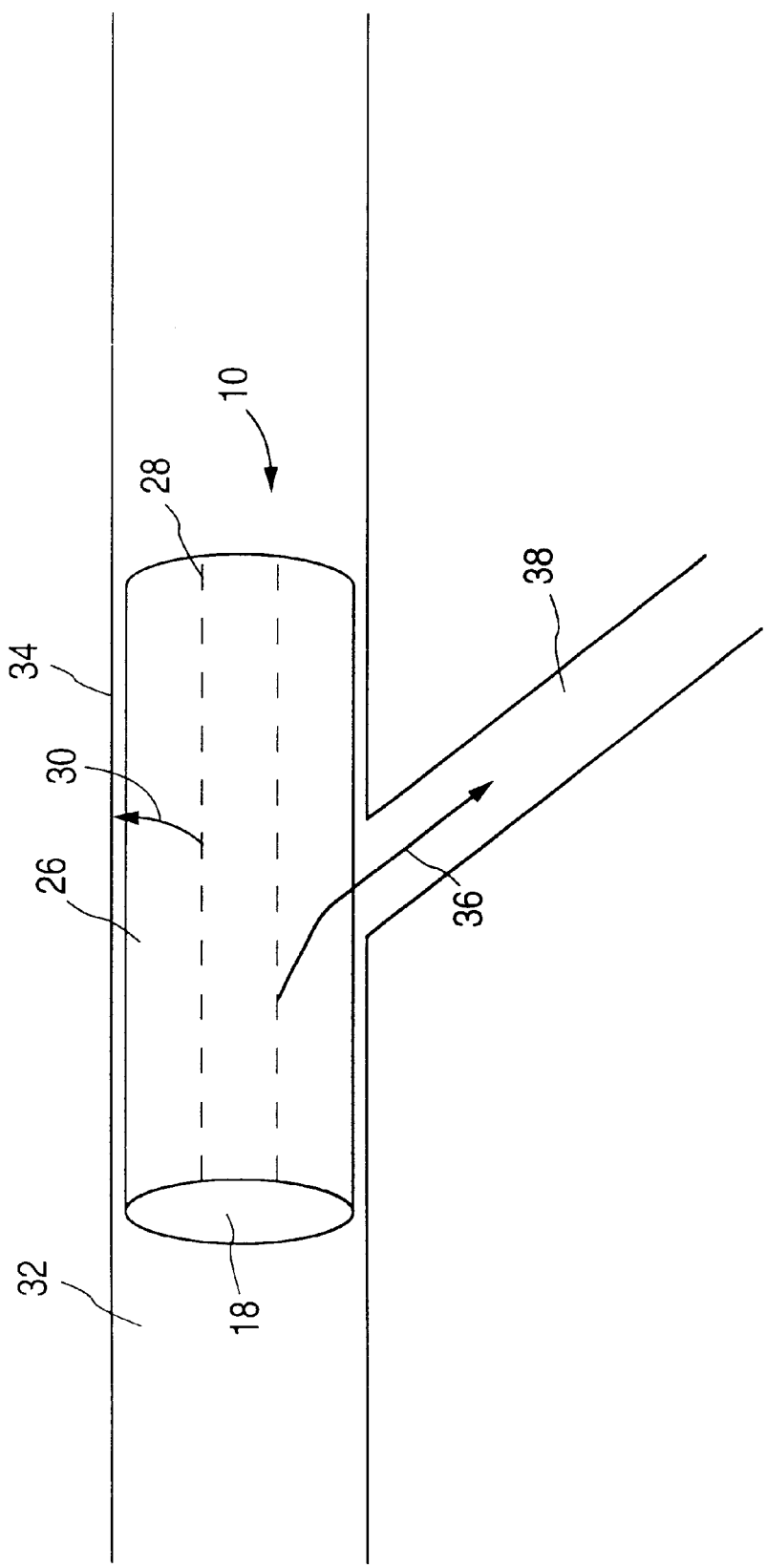
FIG. 6 illustrates exemplary paths of blood flow through interstices within the implantable device of FIG. 5A as employed in a blood vessel.

As depicted in FIG. 6, interstices 28 allow a fluid, such as blood, which flows through central bore 18 to seep through coating 26. Interstices 28 can be selectively patterned to direct the flow of blood in a selected direction, for example in a direction 30 to make contact with a vessel wall 34 of a targeted vessel 32. Such contact between blood and the vessel wall 34 may be required to allow vessel wall 34 to acquire essential nutrients from red blood cells. Alternatively, interstices 28 can be selectively patterned to direct the flow of blood in a direction 36 and into a side vessel 38. In this manner, the creation of interstices 28 allows branching side vessels 38 to remain patent during treatment of targeted vessel 32 with stent 10.

Optional Topcoat

In some embodiments, a second polymeric coating, or topcoat, is formed onto at least a portion of coating 26 on stent 10. In one such embodiment, the topcoat may function as a rate limiting membrane with respect to an active ingredient contained within coating 26. In another embodiment the topcoat itself may be impregnated with an active ingredient, while coating 26 functions as a primer layer to aid the adhesion of the active-ingredient-containing topcoat to stent 10.

Methods of Use

In accordance with the above-described methods, an active ingredient can be applied to a device, e.g., a stent, retained on the stent during delivery and expansion of the stent, and released at a desired control rate and for a predetermined duration of time at the site of implantation. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, or restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrast agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post insertion angiogram may also be utilized to confirm appropriate positioning.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of forming a coating for a metallic prosthesis, comprising:

depositing a sheath including a thermoplastic polymer over at least a portion of a metallic prosthesis, said prosthesis having a plurality of interconnected struts separated by gaps and a longitudinally extending central bore for allowing a fluid to travel through said prosthesis; and exposing said polymer to a sufficient temperature equal to or greater than the glass transition temperature and not greater than about the melting temperature of said polymer effective to cause said sheath to adhere to said prosthesis to form a coating for said prosthesis.

2. The method of claim 1, wherein said coating covers said gaps underlying said sheath.

3. The method of claim 1, wherein said method further comprises:

removing a portion of said coating positioned over some of said gaps to form a pattern of interstices dispersed between said struts for allowing a fluid that flows through said central bore to seep through said coating.

4. The method of claim 3, wherein said removing is performed by applying a laser discharge to said coating to form said pattern of interstices.

5. The method of claim 1, wherein said polymer comprises polycaprolactone, poly(lactide-co-glycolide), poly(hydroxybutyrate), ethylene vinyl acetate, polyvinyl alcohol or an ethylene vinyl alcohol copolymer.

6. The method of claim 1, wherein said coating is impregnated with an active ingredient for the sustained release of said active ingredient when said prosthesis is implanted in a biological passageway, and wherein said active ingredient is selected from a group of antiproliferative, antineoplastic, antiinflanmatory, antiplatelet, anticoagulant, antifibrin, antithrombin, antimitotic, antibiotic, antioxidant substances and combinations thereof.

7. The method of claim 6, wherein said method further comprises:

forming a rate limiting membrane over said coating.

8. The method of claim 1, wherein said coating contains actinomycin D, docetaxel, or paclitaxel.

9. The method of claim 1, wherein said coating contains a material selected from a group of radioactive isotopes and radiopaque elements.

10. The method of claim 1, wherein said method further comprises:

forming a second coating onto said coating on said prosthesis, wherein said second coating is impregnated with an active ingredient for the sustained release of said active ingredient when said prosthesis is implanted in a biological passageway.

11. A method for increasing an amount of a polymeric coating on a stent having struts separated by gaps, without increasing the thickness of the coating, comprising:

inserting a stent comprising a metallic material and having a plurality of interconnected struts separated by gaps into a sheath including a thermoplastic polymer; and exposing said polymer to a sufficient temperature equal to or greater than the glass transition temperature of said polymer and not greater than about the melting temperature of said polymer effective to cause said sheath to adhere to said stent to form a coating for said stent, wherein said coating covers said struts and said gaps between said struts so as to increase the quantity of said polymeric coating supported by said stent without increasing the thickness of said coating on said stent.

12. The method of claim 11, further comprising:

removing a portion of said coating deposited over at least one of said gaps to create an opening in said coating, wherein the size of said opening is smaller than the size of said gap, and wherein said opening allows a fluid to travel through said coating from within said stent.

13. The method of claim 12, wherein said act of removing comprises:

applying a laser discharge to said coating to create said opening in said coating.

14. The method of claim 11, wherein said polymeric coating comprises an active ingredient to inhibit restenosis.

* * * * *